United States Patent [19]
Iki

[11] Patent Number: 5,883,693
[45] Date of Patent: Mar. 16, 1999

[54] OPHTHALMIC REFRACTOR

[75] Inventor: Yoichi Iki, Tokyo, Japan

[73] Assignee: Nikon Corporation, Tokyo, Japan

[21] Appl. No.: 967,031

[22] Filed: Nov. 10, 1997

[30] Foreign Application Priority Data

Nov. 13, 1996 [JP] Japan ................................. 8-302229

[51] Int. Cl.⁶ ...................................... A61B 3/02
[52] U.S. Cl. ..................... 351/239; 351/237; 351/243
[58] Field of Search ................................ 351/237, 238, 351/239, 240, 243, 246, 222, 205, 200, 244

[56] References Cited

U.S. PATENT DOCUMENTS 4,714,330 12/1987 Hennequin ............................. 351/239

FOREIGN PATENT DOCUMENTS 5-212000  8/1993  Japan .

Primary Examiner—Hung Xuan Dang
Attorney, Agent, or Firm—Vorys, Sater, Seymour and Pease LLP

[57] ABSTRACT

An ophthalmic refractor is constructed to judge whether a visual acuity value of a symbol with a mask is minimum or maximum among values in a selected charts, select a chart containing a symbol indicating a visual acuity value smaller than the minimum visual acuity value when the visual acuity value is judged to be minimum, and select a chart containing a symbol indicating a visual acuity value larger than the maximum visual acuity value when the visual acuity value is judged to be maximum.

8 Claims, 10 Drawing Sheets

OPHTHALMIC REFRACTOR

This application claims the benefit of Japanese Application No. 8-302229, which is hereby incorporated by reference.

BACKGROUND OF THE INVENTION

1. Field of the Invention

The present invention relates generally to an ophthalmic refractor and more particularly to an ophthalmic refractor having an enhanced operability.

2. Related Background Arts

This kind of ophthalmic refractor includes a visual acuity chart presenting device such as a chart projector etc that has a plurality of charts containing symbols indicating different visual acuity values. The visual acuity chart presenting device is constructed to select the chart by inputting a visual acuity value of the symbols through ten keys, which should be shown to a patient.

In recent years, there has hitherto got prevailed an ophthalmic refractor including chart selection keys corresponding to the respective charts, and up- and down-keys for automatically inputting a visual acuity value and automatically selecting a chart in order to enhance the operability when examining a visual acuity of the patient.

In the case of selecting a chart containing Landolt rings indicating visual acuity values of, e.g., 0.4–0.6 by use of the chart selection key, an arbitrary visual acuity value of 0.4 among the values of 0.4–0.6 is displayed on a display unit. Then, the ophthalmic refractor is constructed so that when the displayed visual acuity value is sequentially incremented (such as 0.5, 0.6) by the up- and down-keys, the chart containing the symbol of the visual acuity value 0.7 is automatically presented to the patient even if the chart shown presently contains just the symbol indicating the visual acuity values of 0.6 and less.

Further, the ophthalmic refractor incorporates a function to mask the chart in order to make the patient visually recognize only a specific symbol in the chart presented. The mask is classified into a lengthwise one-column mask, a crosswise one-row mask and a one-character mask, which are movable in predetermined directions by using a mask operation key.

Note that the visual acuity value displayed on the display unit is stored as an ophthalmic result.

In the ophthalmic refractor having the above-described up- and down-keys and the mask operation key, the chart is masked so that the patient visually recognizes the symbol of the visual acuity value 0.4, and thereafter the visual acuity value is updated by the up- and down-keys. For example, when the visual acuity value is updated from 0.4 to 0.5, the updating process of the visual acuity value must be done by the up- and down-keys, and the mask has to be moved to a symbol by the mask operation key, which mark should be visually recognized by the patient. The operations of both of the up- and down-keys and the mask operation key on the occasion of the eye examination involving the use of the mask, might conduce to problems in which an eye examining time increases, and besides the operation becomes troublesome. Further, it might happen that the operation by the up- and down-keys gets misconceived as the operation by the mask operation key, which leads to a possibility in which the updated visual acuity value is not coincident with the symbol that should be visually recognized by the patient.

Furthermore, according to the ophthalmic refractor including the up- and down-keys for the visual acuity values, the operation of the up- and down-keys is invariably interlocked with the visual acuity chart operating device, and hence only the chart can not be arbitrarily selected without updating the visual acuity value.

Further, if the visual acuity values of the symbols contained in the charts are limited to 0.1, a displayable visual acuity value is also limited to 0.1, and it is impossible to perform the eye examination for visual acuity values smaller than 0.1.

SUMMARY OF THE INVENTION

It is a primary object of the present invention to provide an ophthalmic refractor capable of giving a high operability to an operator.

To accomplish the above object, according to one aspect of the present invention, an ophthalmic refractor comprises a chart selecting device which selects an arbitrary chart out of a plurality of charts containing symbols indicating a plurality of different visual acuity values, a mask operating device which drives a mask to select an arbitrary symbol among the symbols contained in the chart selected by the chart selecting device and operates the mask in such a direction that the visual acuity value of the symbol is incremented or decremented, a judging device which judges whether the visual acuity value of the symbol selected by the mask is minimum or maximum in the chart selected by the chart selecting device, and a control device which controls the chart selecting device so as to select, when the mask operating device is operated in such a direction that the visual acuity value is decremented if the judging device judges that the visual acuity value is minimum, a chart containing a symbol indicting a visual acuity value smaller than this minimum visual acuity value, and for controlling the chart selecting device so as to select, when the mask operating device is operated in such a direction that the visual acuity value is incremented if the judging device judges that the visual acuity value is maximum, a chart containing a symbol indicating a visual acuity value larger than this maximum visual acuity value.

According to the present invention, the chart can be exchanged by the mask operating device, and therefore the operability can be enhanced.

According to a preferable mode, the judging device has a data table device for storing the different visual acuity values per chart, and judges from the visual acuity values stored in the data table device whether the visual acuity value of the symbol selected by the mask is minimum or maximum in the selected chart.

According to a preferable mode, the ophthalmic refractor further comprises a display device which displays the visual acuity value of the symbol selected by the mask, and an updating device which updates the visual acuity value interlocking with the mask moved by the operation of the mask operating device.

According to another aspect of the present invention, an ophthalmic refractor comprises a chart selecting device which selects an arbitrary chart out of a plurality of charts containing symbols indicating different visual acuity values, a display device which displays a visual acuity value of a symbol contained in the chart selected by the selecting device, an operating device which increments or decrements the visual acuity value displayed on the display device, a control device which controls the chart selecting device so as to select a chart containing a symbol indicating the incremented or decremented visual acuity value, interlocking with the increment or decrement of the visual acuity value operated by the operating device, a masking device which drives a mask to select an arbitrary symbol among the symbols contained in the chart selected by the chart selecting device, and an interlocking device which moves the mask in such a direction that the visual acuity value corresponding to the symbol selected by the mask is incremented or decremented interlocking with the increment or decrement of the displayed visual acuity value caused by the operating device when the arbitrary symbol is selected by the masking device.

According to the present invention, the symbol that should be visually recognized by the patient is invariably coincident with the visual acuity value displayed on the display device, thereby eliminating an operation mistake and enhancing the operability.

According to a preferable mode, the ophthalmic refractor further comprises a releasing device which releases the interlocking of the increment or decrement of the visual acuity value operated by the operating device with the movement of the mask.

According to the present invention, the operator is able to make an arbitrary selection as to whether or not the interlocking is done, and therefore the operability is enhanced.

According to still another aspect of the present invention, an ophthalmic refractor comprises a chart selecting device which selects an arbitrary chart out of a plurality of charts containing symbols indicating different visual acuity values, a display device which displays a visual acuity value of a symbol contained in the arbitrary chart, an operating device which increments or decrements the visual acuity value displayed on the display device, a control device which controls the chart selecting device so as to select, when the operating device increments or decrements the visual acuity value, a chart containing the symbol indicating the incremented or decremented visual acuity value, and a interlock selecting device which makes a selection as to whether or not the operating device should be interlocked with the chart selecting device.

According to the present invention, the operator is able to make an arbitrary selection as to whether or not the interlocking is done, and therefore the operability is enhanced.

According to a further aspect of the present invention, an ophthalmic refractor comprises a chart selecting device which selects an arbitrary chart out of a plurality of charts containing symbols indicating different visual acuity values, a display device which displays a visual acuity value of a symbol contained in the arbitrary chart, an operating device which increments or decrements the visual acuity value displayed on the display device, and a control device which inhibits the display device to display the visual acuity value till the operating device increments or decrements the visual acuity value after selecting the arbitrary chart.

According to the present invention, only when the operator needs to confirm the visual acuity value, the visual acuity value is displayed, and inputted and hence the operability is enhanced.

According to a still further aspect of the present invention, an ophthalmic refractor comprises a chart selecting device which selects an arbitrary chart out of a plurality of charts containing symbols indicating different visual acuity values, a display device which displays a visual acuity value of a symbol contained in the arbitrary chart, an operating device which increments or decrements the visual acuity value displayed on the display device, a control device which controls the chart selecting device so as to select, when the operating device increments or decrements the visual acuity value, a chart containing a symbol indicating the visual acuity value incremented or decremented, a judging device which judges whether or not the visual acuity value displayed on the display device is the minimum value among the visual acuity values of the symbols contained in the plurality of charts, and an inputting device which can input visual acuity values smaller than the minimum value judged by the judging device when the judging device judges that the visual acuity value is minimum and when the operating device further decrements the visual acuity value.

According to the present invention, even when the visual acuity value of the symbol contained in the chart comes to a lower limit, visual acuity values smaller than that value can be inputted.

BRIEF DESCRIPTION OF THE DRAWINGS

Other objects and advantages of the present invention will become apparent during the following discussion in conjunction with the accompanying drawings, in which.

DESCRIPTION OF THE PREFERRED EMBODIMENTS

Figure 1:
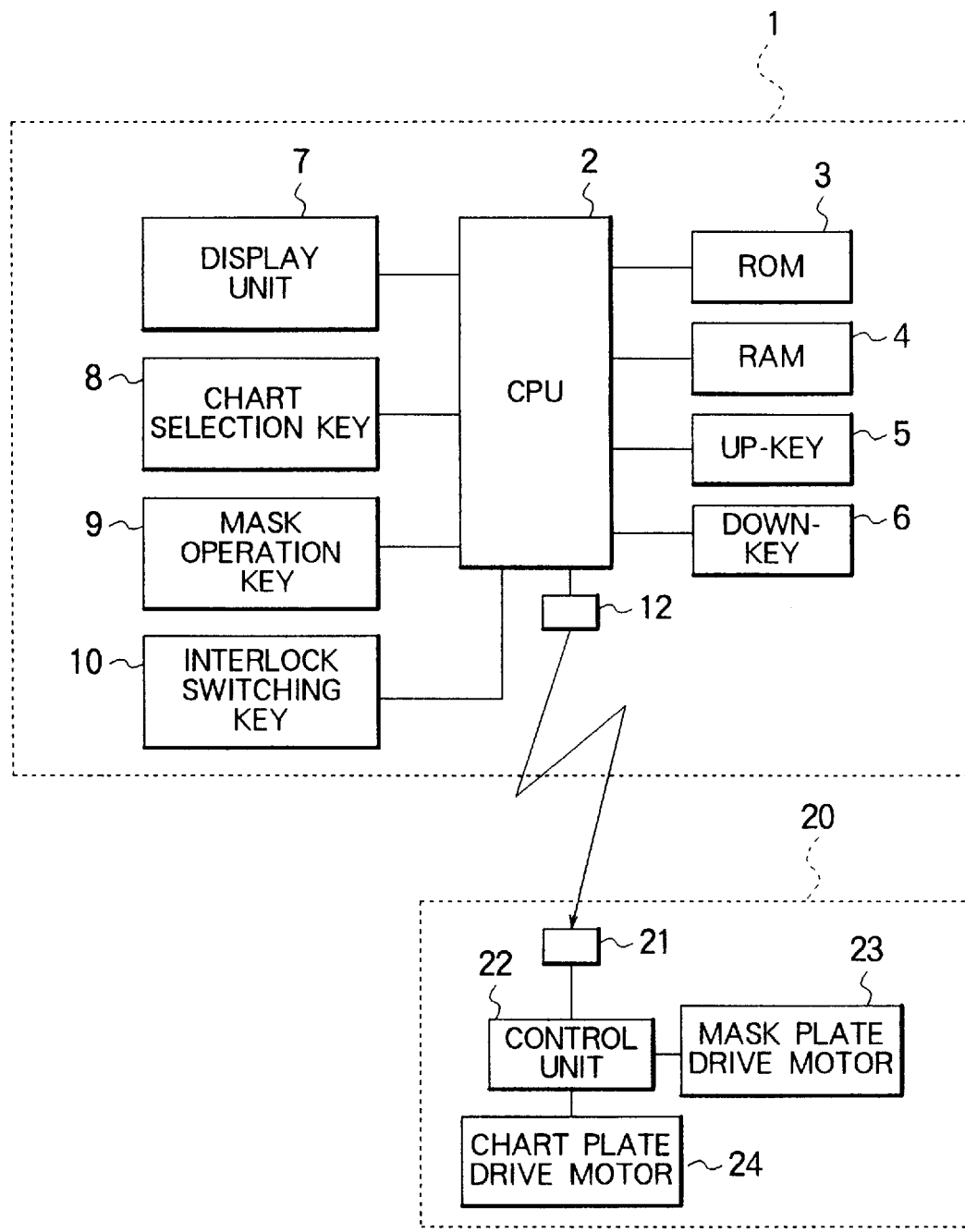
FIG. 1 is a diagram showing a whole construction according to the present invention.

FIG. 1 is a block diagram showing constructions of an ophthalmic refractor body 1 and of a visual acuity chart presenting device 20. The ophthalmic refractor body 1 is disposed in front of an eye to be examined, and includes a lens chamber (unillustrated) having a plurality of optical lenses and a filter that are used for an eye examination. The visual acuity chart presenting device 2 includes charts having symbols for examining a visual acuity of a patient, and a mask for helping the patient visually recognize only a predetermined symbol.

The ophthalmic refractor body 1 includes a ROM 3 stored with a ophthalmic procedure program for examining the eye of the patient, a RAM 4 containing a work area for a control circuit 2 performing a variety of calculations by using ophthalmic data, and a display unit 7 for displaying the ophthalmic data (a spherical power, a cylindrical power, a cylindrical axis and a visual acuity value etc) of the eye examined. The ophthalmic refractor body 1 also includes an up-key 5 for incrementing (up-input) the visual acuity value displayed on the display unit 7, a down-key 6 for decrementing (down-input) the visual acuity value displayed on the display unit 7, chart selection keys 8 marked with characters and pictorial designs as the symbols in the respective charts possessed by the visual acuity chart presenting device 2 and provided corresponding to the respective charts, a mask operation key unit 9 for overlapping a mask pattern on an arbitrary symbol in the chart shown to the patient and exchanging the mask pattern, an interlock switching key 10 for switching an interlocking process of the operations of the up-key 5 and the down-key 6 and also the chart selection in the visual acuity chart presenting device 20, and a transmitting unit 12 for transmitting code signals based on infrared-rays to a receiving unit 21 of the visual acuity chart presenting device 20. The ROM 3 has a data table stored with the visual acuity values of the symbols of the charts possessed by the visual acuity chart presenting device 20 which will be mentioned later on, corresponding to the respective charts.

The mask operation key unit 9 has a crosswise one row operation key for selecting a crosswise one-row mask, a lengthwise one-column operation key for selecting a lengthwise one-column mask, and a one-character key for selecting a one-character mask.

The ophthalmic refractor body 1 further includes the control circuit 2 for controlling the display unit 7 and the visual acuity chart presenting device 20 on the basis of the respective keys 5, 6, 8, 9 and 10. An operation of this control circuit 2 will be hereinafter be described.

Figure 2:
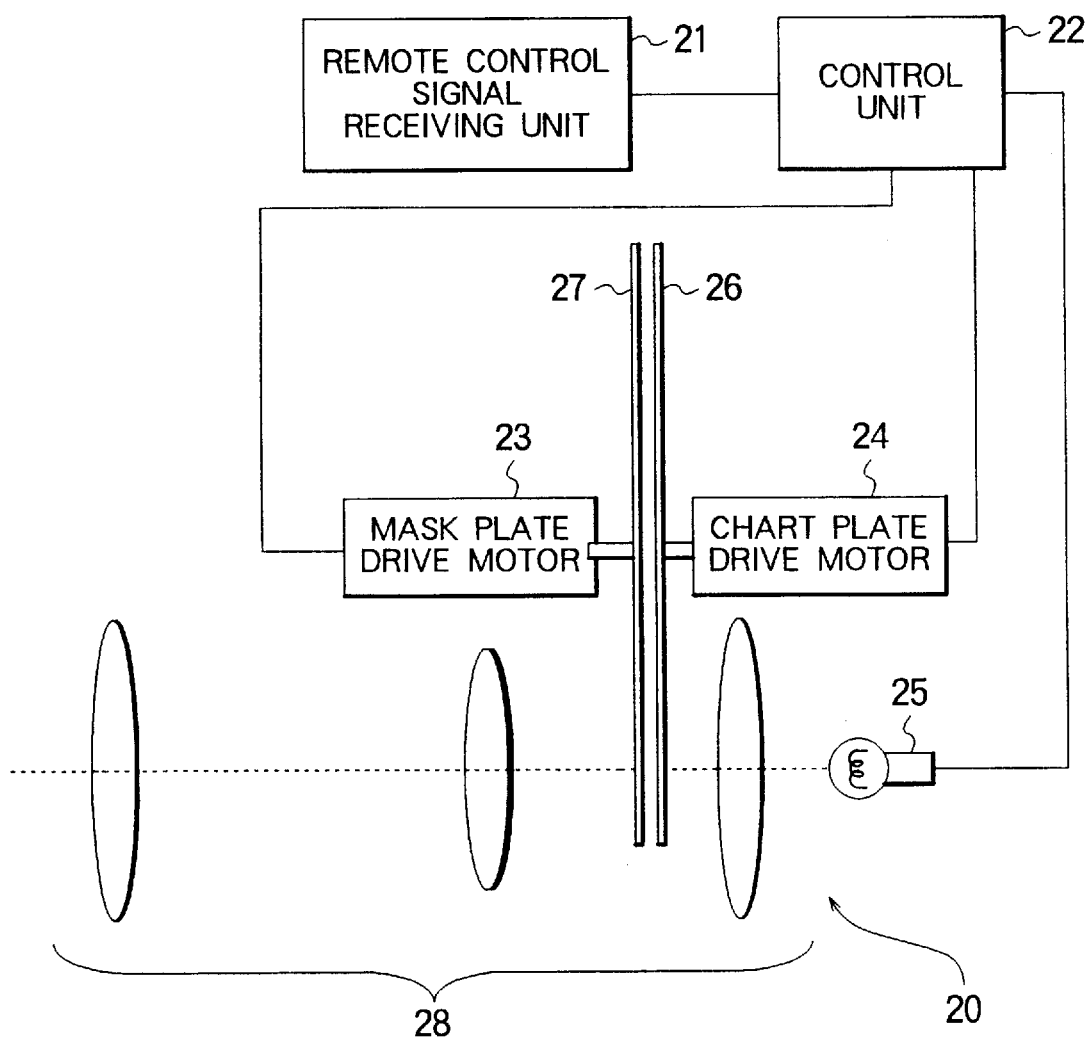
FIG. 2 is a diagram showing a construction of a visual acuity chart presenting device according to the present invention.
Figure 3:
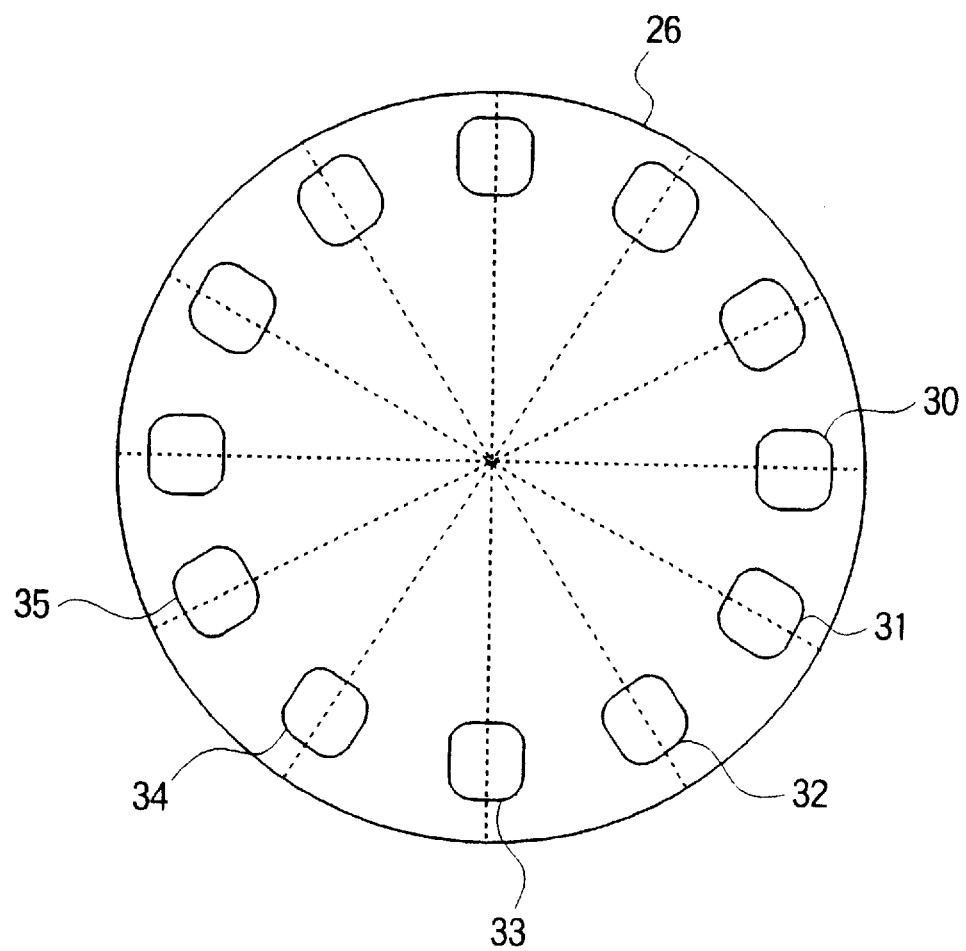
FIG. 3 is a view illustrating a chart plate of the visual acuity chart device according to the present invention.
Figure 4A:
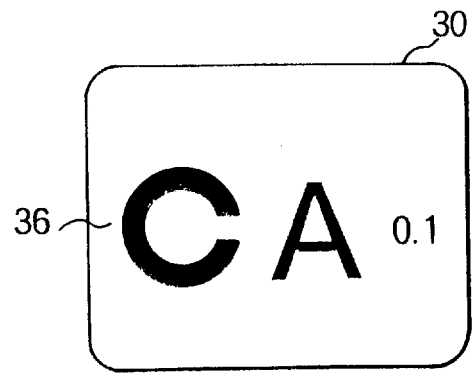
FIGS. 4A–4D are diagrams showing visual acuity measuring charts for adults.
Figure 4B:
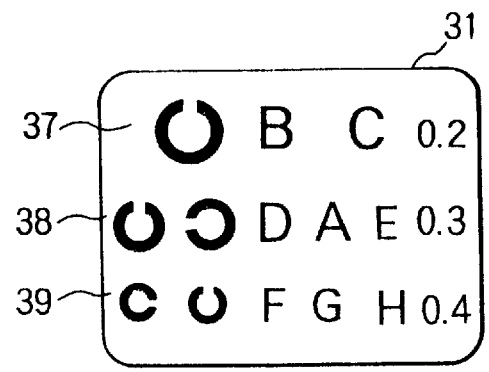
Figure 4C:
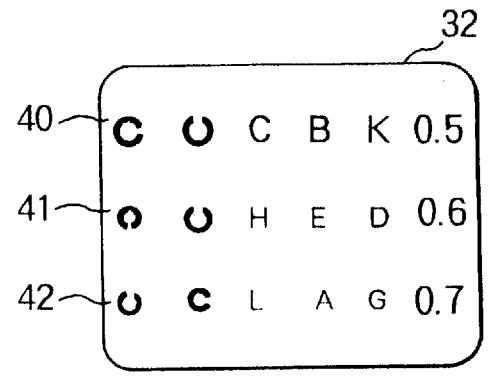
Figure 4D:
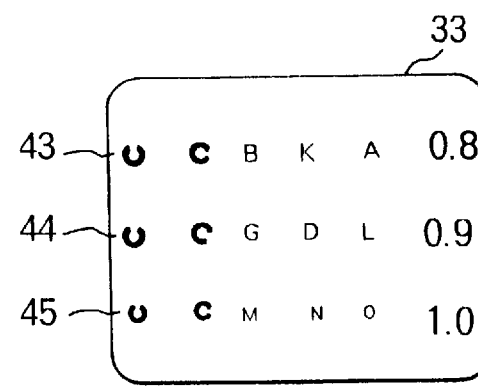
Figure 5A:
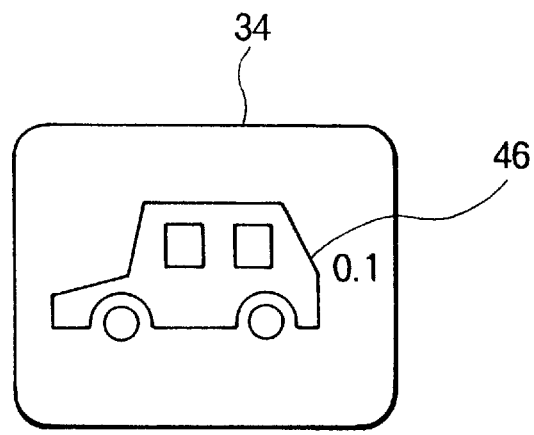
FIGS. 5A and 5B are diagrams showing visual acuity measuring charts for infants.
Figure 5B:
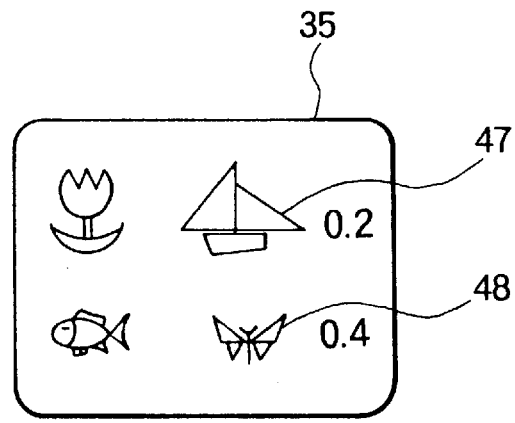

On the other hand, the visual acuity chart presenting device 20 has, as illustrated in FIG. 2, a chart plate 26 and a maskplate 27. Adult visual acuity charts 30–33 shown in FIGS. 4A–4D and infant visual acuity charts 34, 35 shown in FIGS. 5A and 5B, are disposed on the chart plate 26 at equal intervals in the circumferential direction as illustrated in FIG. 3. The adult visual acuity charts are charts 30, 31, 32 and 33. The chart 30 has, as shown in FIG. 4A, symbols 36 such as a Landolt ring indicating a visual acuity value of 0.1. The chart 31 has, as shown in FIG. 4B, symbols 37–39 such as Landolt rings indicating visual acuity values of 0.2–0.3. The chart 32 has, as shown in FIG. 4C, symbols 40–42 such as Landolt rings indicating visual acuity values of 0.5–0.7. The chart 33 has, as shown in FIG. 4D, symbols 43–45 such as Landolt rings indicating visual acuity values of 0.8–1.0. Further, the infant charts include a pictorial design symbol 46 indicating the visual acuity value of 0.1 as illustrated in FIG. 5A, and pictorial design symbols 47, 48 indicating the visual acuity values of 0,2 and 0.4 as illustrated in FIG. 5B. Note that in addition to the adult visual acuity charts shown in FIGS. 4A–4D and the infant visual acuity charts shown in FIGS. 5A and 5B, a variety of designs for measuring the cylindrical power and measuring a balance between two eye, are disposed along the circumference on the chart plate 26.

Figure 6A:
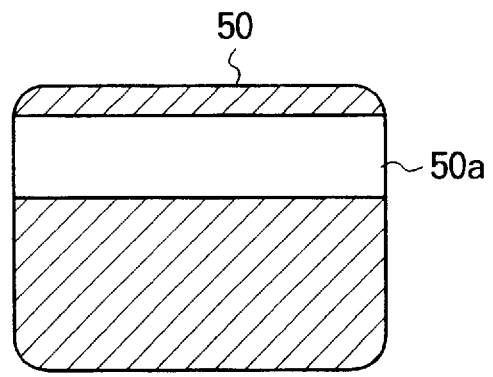
FIGS. 6A–6C are diagrams showing crosswise one-row mask patterns.
Figure 6B:
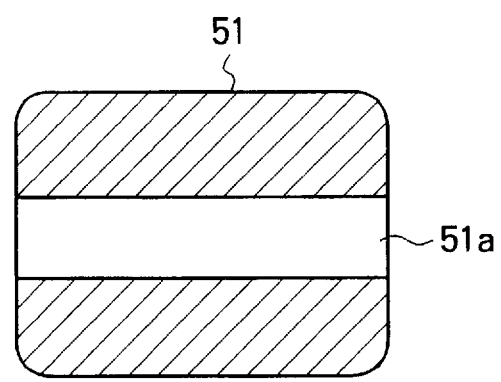
Figure 6C:
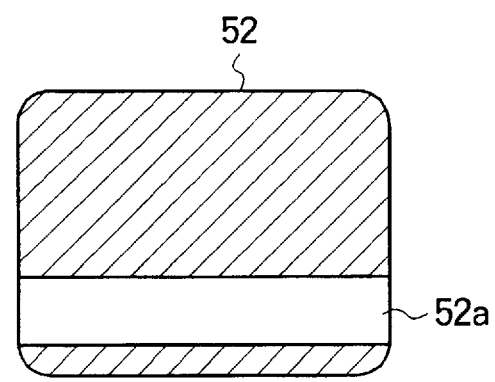
Figure 7A:
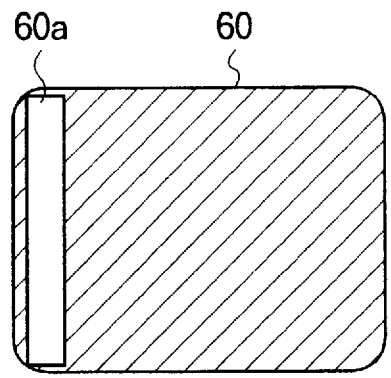
FIGS. 7A–7C are diagrams showing lengthwise one-column mask patterns.
Figure 7B:
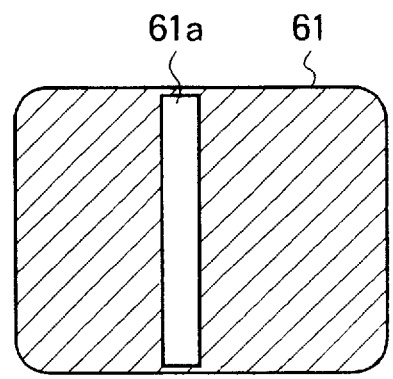
Figure 7C:
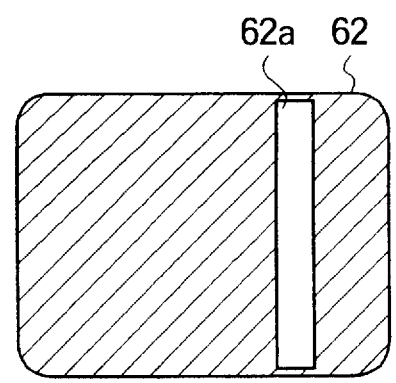
Figure 8A:
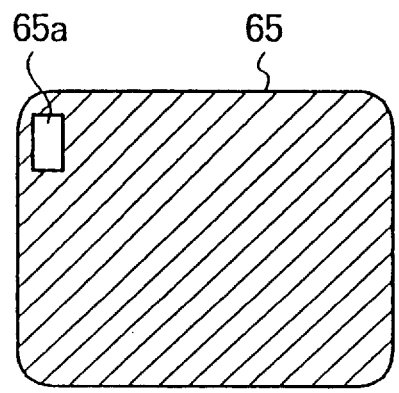
FIGS. 8A and 8B are diagrams showing one-character mask patterns.
Figure 8B:
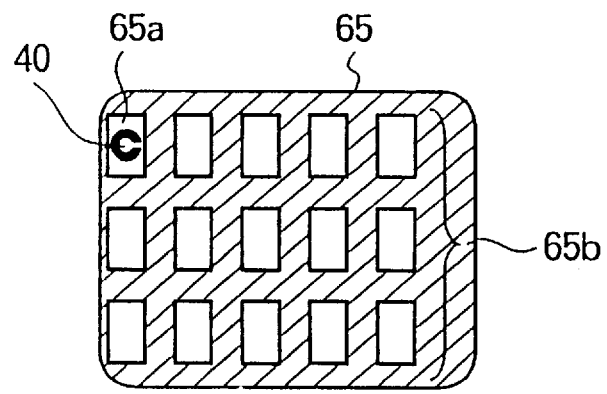

Disposed in the circumferential direction on the mask plate 27 are crosswise one-row mask patterns 50–52 containing transparent portions 50a–52a as illustrated in FIGS. 6A–6C, lengthwise one-column mask patterns 60–62 containing light transparent portions 60a–62a as shown in FIGS. 7A–7C, and a one-character mask pattern 65 containing light transparent portions 65a, 65b as illustrated in FIGS. 8A and 8B. Note that the mask plate 27 includes, other than those shown in FIGS. 6–8, crosswise one-row mask patterns, lengthwise one-column mask patterns and one-character mask patterns, which contain transparent portions corresponding to the respective symbols included in the charts.

The visual acuity chart presenting device 20 comprises, as illustrated in FIGS. 1 and 2, the receiving unit 21 for receiving the code signals transmitted by the transmitting unit 12 of the ophthalmic refractor body 1, a chart plate drive motor 24 for driving the chart plate 26, a mask plate drive motor 23 for driving the mask plate 27, a control unit 22 for controlling the mask plate drive motor 23 and the chart plate drive motor 24 on the basis of the code signals received by the receiving unit 21, a light source 25 composed of a halogen lamp for illuminating the charts on the chart plate 26 from back side, and a projection lens system 28 for projecting the thus illuminated charts.

Figure 9:
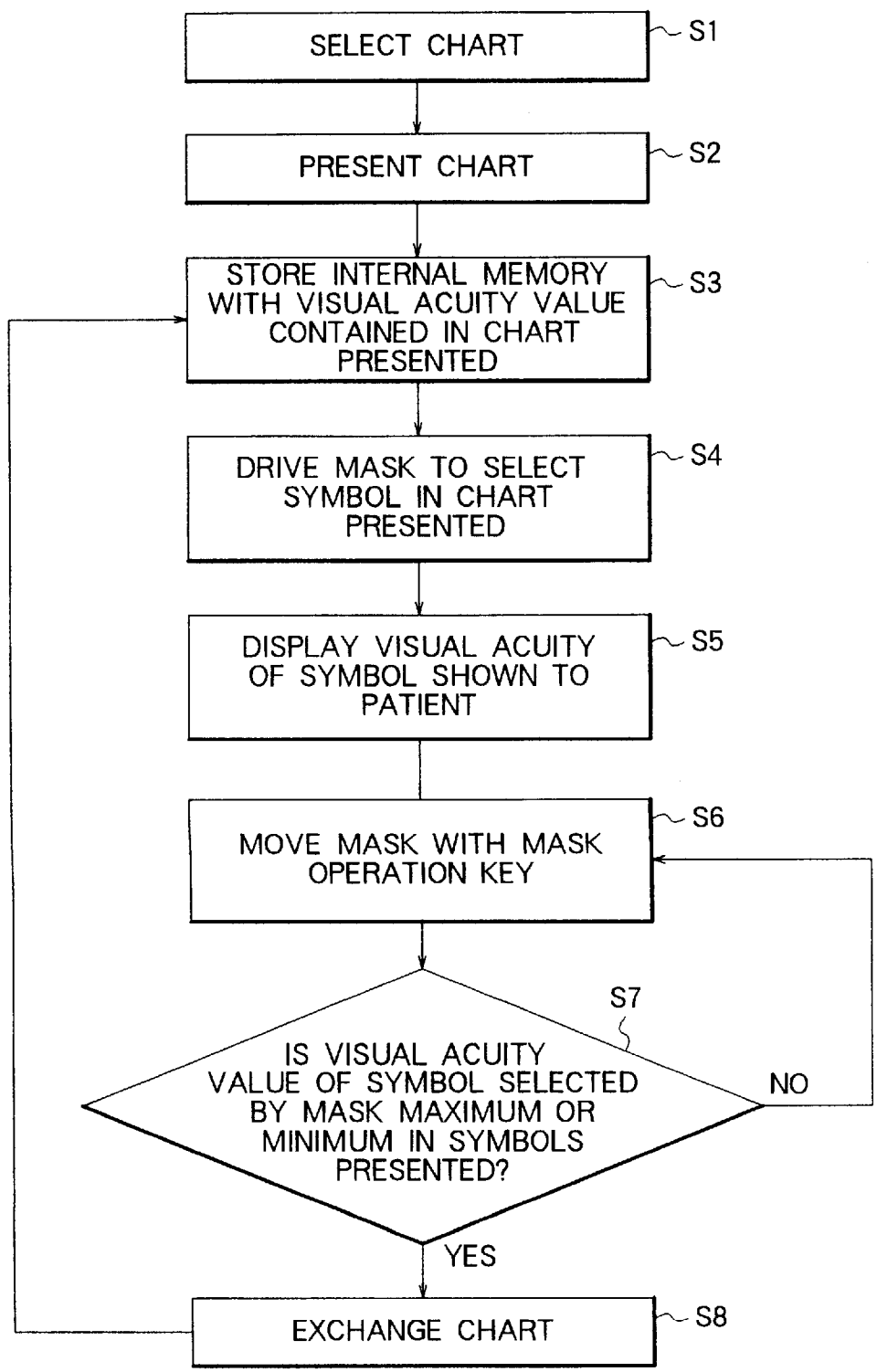
FIG. 9 is a flowchart showing operations of a control circuit in a first embodiment.

Next, an operation of the control circuit 2 of the ophthalmic refractor body 1 in accordance with a first embodiment, will be explained with reference to a flowchart shown in FIG. 9.

An eye operator a chart containing a symbol indicating a visual acuity value to be shown to the patient when measuring a visual acuity value of the patient by pushing one of the plurality of chart selection keys 8 (step S1).

The control circuit 2, when the chart selection key 8 is selected, makes the transmitting unit 12 transmit a code signal representing that chart so as to present the chart corresponding to the pushed selection key 8. The visual acuity chart presenting device 20 makes the receiving unit 21 receive the code signal transmitted from the transmitting unit 12 of the ophthalmic refractor body 1. The control unit 22 of the visual acuity chart presenting device 20 decodes the code signal received by the receiving unit 21, and drives the chart plate drive motor 24 so that the chart indicated by that code signal is presented (step S2).

Further, when the chart selection key 8 is pushed, the visual acuity values of the symbols possessed by the selected chart 33 are read from the data table of the ROM 3 and stored in an internal memory incorporated into the control circuit 2. For example, when the chart 23 shown in FIG. 4C is selected, the visual acuity values indicated by the symbols contained in this chart 32 are three values, i.e., 0.5, 0.6 and 0.7, and these three values will be stored in the internal memory RAM 4 (step S3).

Then, when the operator manipulates the mask operation key unit 9, only a symbol 40 of the visual acuity value 0.5 in the chart 32 selected, is shown. Namely, the control circuit 2, when the crosswise one-row operation key of the mask operation key unit 9 is pushed, causes the transmitting unit 12 to transmit the code signal representing a mask pattern 50 so that the mask pattern 50 for showing only the symbol indicating the minimum visual acuity value (0.5 in the case of the chart 32) is superposed on the chart 32. In the visual acuity chart presenting device 20, the receiving unit 21 receives the code signal transmitted from the transmitting unit 12 of the ophthalmic refractor body 1. The control unit 22 of the visual acuity chart presenting device 20 decodes the code signal received by the receiving unit 21, and drives the mask plate drive motor 23 so that the mask pattern indicated by that code signal is presented. Note that when the mask operation key 9 is pushed, the driving process may be done so that the mask pattern to be selected is not the mask pattern 50 for showing only the symbol indicating the minimum visual acuity value (0.8 in the case of the chart 33) but a mask pattern 52 for showing only the symbol indicating the maximum visual acuity value (step S4).

The control circuit 2 calls from the internal memory the visual acuity value of 0.5 corresponding to the symbol shown to the patient, and causes the display unit 11 to display the visual acuity value of 0.5 (step S5). Then, the mask pattern is exchanged in a sequence of the mask pattern 50, the mask pattern 51 and the mask pattern 52 by manipulating the crosswise one-row operation key of the mask operation key unit 9, whereby the symbols of the visual acuity values 0.5, 0.6 and 0.7 are sequentially shown to the patient. At this time, the control circuit 2 updates the visual acuity value corresponding to the symbol shown to the patient by manipulating the crosswise one-row operation key. On the display unit 11, the visual acuity values displayed each time is exchanged in the sequence of the mask patterns 50, 51 and 52, also change to 0.5, 0.6 and 0.7. (step S6).

The control circuit 2 judges whether the visual acuity value of the symbol with the mask pattern is maximum or minimum in the chart. For instance, if the chart 32 shown in FIG. 4C, on which the mask pattern 52 shown in FIG. 6A is superposed, is displayed to the patient, the symbol of the visual acuity value 0.5 is shown. Herein, the operator asks the patient "Can you read this symbol?", and the patient answers "Yes, I can.", in which case the processing returns to step S6, and the operator further manipulates the crosswise one-row operation key. That is to say, the operator executes the operation that the symbol of the next visual acuity value 0.6 should be shown to the patient by use of the mask operation key unit 9. Then, the mask pattern shown in FIG. 6B is superposed on the chart 32, thereby showing the symbol of the visual acuity value 0.6. Furthermore, when the patient answers "I can read" the symbol of the visual acuity value 0.6 too, the processing again returns to step S6. Then, the mask pattern 52 shown in FIG. 6C is superposed on the chart 32 by manipulating the mask operation key unit 9, whereby the symbol 42 of the visual acuity value 0.7 is shown to the patient. Herein, the operator again asks the patient "Can you read this symbol?", and the patient answers "Yes, I can.", in which case the operator further manipulates the crosswise one-row operation key. Namely, the operator, it follows, performs the operation that the symbol 43 of the next visual acuity value 0.8 should be shown to the patient. Herein, the control circuit 2 judges from the values stored in the internal memory that the symbol 42 visually recognized at present by the patient indicates the maximum visual acuity value in the chart presented (step S7).

Further, the symbol of the visual acuity value 0.5 is shown to the patient by superposing the mask pattern 50 on the chart 32. Then, the operator asks the patient "Can you read this symbol?", and the patient answers "No, I can't.", in which case the operator manipulates the mask operation key unit 9 so that the symbol 39 of the visual acuity value 0.4 is shown to the patient.

Then, the control circuit 2 judges from the visual acuity values stored in the internal memory that the visual acuity value of 0.5 of the symbol 40 visually recognized at present by the patient is the minimum visual acuity value in the chart presented (step S7).

As a result of the judgement made by the control circuit 2, if it is judged that the visual acuity value of the symbol visually recognized by the patient is the maximum value, the control circuit 2 makes the transmitting unit 12 transmit to the receiving unit 21 the code signal indicating that the chart 33 containing the symbol 43 of the visual acuity value 0.8 should be presented. The control unit 22 of the visual acuity chart presenting device 20 decodes the code signal received by the receiving unit 21, and drives the chart plate drive motor 24 so as to display the chart 33 indicated by that code signal (step S8). Then, the visual acuity value of the symbol contained in the chart is stored in the RAM 4 (step S3). Further, the mask plate drive motor 23 is driven so that the mask pattern 50 is superposed on the chart 33 to show only the symbol 43 of the visual acuity value 0.8 (step S4). The control circuit 2 that has transmitted the code signal reads from the ROM 3 the data table having the chart containing the symbol 43 of the visual acuity value 0.8, and stores the internal memory with the visual acuity value stored in this data table. Then, the visual acuity value of 0.8 is displayed on the display unit 7, and thus displayed visual acuity value of 0.8 is stored in the RAM 4 (step S5).

Note that the chart is exchanged by manipulating the mask operation key unit 9 when the visual acuity value is moved in an up- or down-direction with respect to the crosswise one-row operation and the one-character operation. In the case of the lengthwise one-column operation, only the movement of the mask may be carried out.

Further, on the assumption that an interlocking process between the movement of the mask pattern and the exchange of the chart might be trouble some to some operator, the ophthalmic refractor body 1 includes the interlock switching key 10 for switching as to whether to effect the interlocking process.

Figure 10:
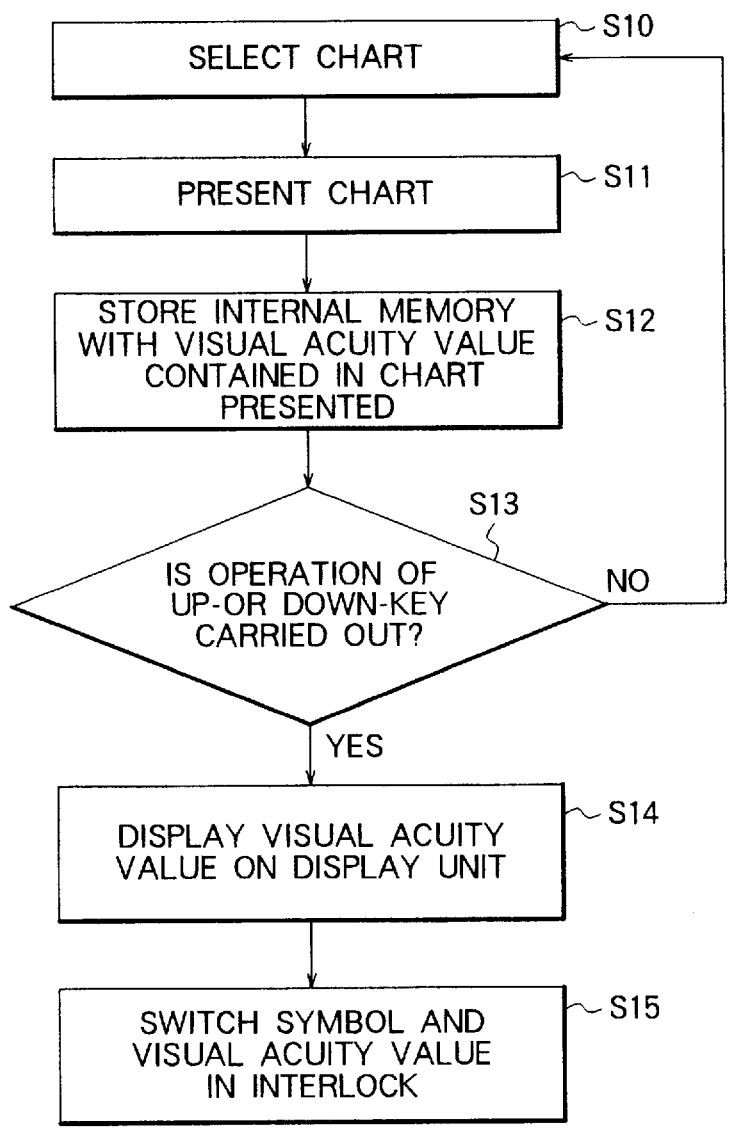
FIG. 10 is a flowchart showing operations of the control circuit in a second embodiment.

An operation of the control circuit 2 of the ophthalmic refractor body 1 in accordance with a second embodiment will be explained with reference to a flowchart shown in FIG. 10. Note that the constructions of the ophthalmic refractor body 1 and the visual acuity chart presenting device 20 are the same as those described above, and hence the explanations thereof are omitted. The second embodiment is based on the operations of the visual acuity value up-key 5 and of the visual acuity value down-key 6 without using the mask operation key unit 9. Steps S10, S11 and S12 are the same as steps S1, S2 and S3 that have been described above, and therefore the explanations thereof are omitted.

The control circuit 2 judges whether or not the visual acuity value up-key 5 or the visual acuity value down-key 6 is pushed (step S13).

If the control circuit 2 judges that the visual acuity value up-key 5 or the visual acuity value down-key is not manipulated, the processing returns to step S10, and the chart may be selected again by the chart selection key 8. Further, if the control circuit 2 judges that the up-key 5 or the down-key 6 is manipulated, the control circuit 2 causes the display unit 11 to display the visual acuity value of 0.5 corresponding to the symbol 40 contained in the chart 32, and makes the RAM 4 store this visual acuity value (step S14).

After the visual acuity value has been displayed on the display unit 11, every time the visual acuity value up-key 5 or the visual acuity value down-key 6 is manipulated, the visual acuity value displayed in the display unit 11 and the visual acuity value stored in the RAM 4, are updated, and also the code signal is transmitted to the visual acuity chart presenting device 20 to show the chart that should be presented to the patient. Namely, the control circuit 2 judges whether the visual acuity value of the symbol displayed at present is maximum or minimum among the visual acuity values of the symbol contained in that chart. For example, the operator asks the patient "Can you read the middle symbol?" in the chart 32 shown in FIG. 4C, and the patient answers "Yes, I can", at which time the operator further manipulates the visual acuity value up-key. Then, the visual acuity value of 0.7 is displayed on the display unit 11 and then stored in the RAM 4. Next, the operator asks the patient "Can you read the lowest symbol?" in the chart 32 shown in FIG. 4C, and the patient answers "Yes, I can", at which time the operator further manipulates the visual acuity value up-key. Then, the visual acuity value of 0.8 is displayed on the display unit 11 and stored in the RAM 4. Herein, the control circuit 2 judges from the visual acuity values stored in the internal memory that the no symbol to be next shown to the patient exists in the chart 32, and transmits the code signal to the visual acuity chart presenting device 20 so as to replace the chart 32 with the chart 33 having the symbol 43 of the visual acuity value 0.8 to be next shown thereto. Upon receiving this code signal, the visual acuity chart presenting device 20 drives the chart plate drive motor 24 to show the chart 33 (step S15).

Whereas if given an answer of being unable to read the symbol of the visual acuity value 0.5, the visual acuity value of 0.5 is displayed on the display unit 7, in which state the visual acuity value down-key 6 is further manipulated. At this time, the control circuit 2 makes the transmitting unit 12 transmit the code signal in order to show the chart 31 containing the symbol 39 of a smaller visual acuity value 0.4 than the visual acuity value 0.5 corresponding to the symbol 40 shown at the present, and the visual acuity chart presenting device exchanges it with the chart 31. The visual acuity value 0.4 corresponding to the selected symbol is displayed on the display unit 7 and then stored in the RAM 4 (step S5).

Moreover, the control circuit 2, when the chart 30 is presented by manipulating the visual acuity value down-key 6, and if the patient is unable to recognized the visual acuity value of 0.1 of the symbol 36 contained in the chart 30, comes to such an assumption that a simple ophthalmic process should be executed by decreasing a distance between the symbol and the patient.

In this case, the control circuit 2 judges that the visual acuity value of 0.1 of the symbol 36 in the chart 30 possessed by the visual acuity chart presenting device 20 is minimum and that the visual acuity value down-key 6 is manipulated, and there may be provided a contrivance capable of inputting visual acuity values smaller than 0.1. Thus, if the visual acuity value contained in the chart comes to a limit, the ROM 3 is previously prepared with visual acuity values excluding the visual acuity values of the symbols contained in the chart, and, when the control circuit 2 judges that the visual acuity value of the symbol in the chart possessed by the visual acuity chart presenting device 20 is minimum and that the visual acuity value down-key 6 is manipulated, a contrivance may be such that the visual acuity values smaller than the visual acuity values corresponding to the symbol are displayed on the display unit 11 and stored in the RAM 4.

Further, on the assumption that the interlocking process of the manipulations of the visual acuity value up- and down-keys 5, 6 and the exchange of the chart might be troublesome, the ophthalmic refractor body 1 includes the interlock switching key 10 for switching as to whether or not the interlocking process should be done.

It is apparent that, in this invention, a wide range of different working modes can be formed based on the invention without deviating from the spirit and scope of the invention. This invention is not restricted by its specific working modes except being limited by the appended claims.

What is claimed is:

1. An ophthalmic refractor comprising:
   a chart selecting device which selects an arbitrary chart out of a plurality of charts containing symbols indicating different visual acuity values;
   a mask operating device which drives a mask to select an arbitrary symbol among the symbols contained in the chart selected by said chart selecting device and operates the mask in such a direction that the visual acuity value of the symbol is incremented or decremented;
   a judging device which judges whether the visual acuity value of the symbol selected by the mask is minimum or maximum in the chart selected by said chart selecting device; and
   a control device which controls said chart selecting device so as to select, when said mask operating device is operated in such a direction that the visual acuity value is decremented if said judging device judges that the visual acuity value is minimum, a chart containing a symbol indicting a visual acuity value smaller than this minimum visual acuity value, and for controlling said chart selecting device so as to select, when said mask operating device is operated in such a direction that the visual acuity value is incremented if said judging device judges that the visual acuity value is maximum, a chart containing a symbol indicating a visual acuity value larger than this maximum visual acuity value.

2. The ophthalmic refractor according to claim 1, wherein said judging device has a data table device for storing the different visual acuity values per chart, and judges from the visual acuity values stored in said data table device whether the visual acuity value of the symbol selected by the mask is minimum or maximum in the selected chart.

3. The ophthalmic refractor according to claim 2 further comprising:
   a display device which displays the visual acuity value of the symbol selected by the mask; and
   an updating device which updates the visual acuity value interlocking with the mask moved by the operation of said mask operating device.

4. An ophthalmic refractor comprising:
   a chart selecting device which selects an arbitrary chart out of a plurality of charts containing symbols indicating different visual acuity values;
   a display device which displays a visual acuity value of a symbol contained in the chart selected by said selecting device;
   an operating device which increments or decrements the visual acuity value displayed on said display device;
   a control device which controlls said chart selecting device so as to select a chart containing a symbol indicating the incremented or decremented visual acuity value, interlocking with the increment or decrement of the visual acuity value operated by said operating device;
   a masking device which drives a mask to select an arbitrary symbol among the symbol contained in the chart selected by said chart selecting device; and
   an interlocking device which moves the mask in such a direction that the visual acuity value corresponding to the symbol selected by the mask is incremented or decremented interlocking with the increment or decrement of the displayed visual acuity value caused by said operating device when the arbitrary symbol is selected by said masking device.

5. The ophthalmic refractor according to claim 4, further comprising a releasing device which releases the interlocking of the increment or decrement of the visual acuity value operated by the operating device with the movement of the mask.

6. An ophthalmic refractor comprising:
   a chart selecting device which selects an arbitrary chart out of a plurality of charts containing symbols indicating different visual acuity values;

a display device which displays a visual acuity value of a symbol contained in the arbitrary chart;

an operating device which increments or decrements the visual acuity value displayed on said display device;

a control device which controlls said chart selecting device so as to select, when said operating device increments or decrements the visual acuity value, a chart containing the symbol indicating the incremented or decremented visual acuity value; and a interlock selecting device which makes a selection as to whether or not said operating device should be interlocked with said chart selecting device.

7. An ophthalmic refractor comprising:

a chart selecting device which selects an arbitrary chart out of a plurality of charts containing symbols indicating different visual acuity values;

a display device which displays a visual acuity value of a symbol contained in the arbitrary chart;

an operating device which increments or decrements the visual acuity value displayed on said display device; and a control device which inhibits said display device to display the visual acuity value till said operating device increments or decrements the visual acuity value after selecting the arbitrary chart.

8. An ophthalmic refractor comprising:

a chart selecting device which selects an arbitrary chart out of a plurality of charts containing symbols indicating different visual acuity values;

a display device which displays a visual acuity value of a symbol contained in the arbitrary chart;

an operating device which increments or decrements the visual acuity value displayed on said display device;

a control device which controlls said chart selecting device so as to select, when said operating device increments or decrements the visual acuity value, a chart containing a symbol indicating the visual acuity value incremented or decremented;

a judging device which judges whether or not the visual acuity value displayed on said display device is the minimum value among the visual acuity values of the symbols contained in the plurality of charts; and an inputting device which can input visual acuity values smaller than the minimum value judged by said judging device when said judging device judges that the visual acuity value is minimum and when said operating device further decrements the visual acuity value.

* * * * *